(12) United States Patent
Davies

(10) Patent No.: US 6,696,304 B1
(45) Date of Patent: Feb. 24, 2004

(54) PARTICULATE SOLID PHASE IMMOBILIZED PROTEIN QUANTITATION

(75) Inventor: Travis Parker Davies, Austin, TX (US)

(73) Assignee: Luminex Corporation, Austin, TX (US)

(*) Notice: Subject to any disclaimer, the term of this patent is extended or adjusted under 35 U.S.C. 154(b) by 0 days.

(21) Appl. No.: 09/512,013

(22) Filed: Feb. 24, 2000

Related U.S. Application Data

(60) Provisional application No. 60/121,497, filed on Feb. 24, 1999.

(51) Int. Cl.[7] .............................................. G01N 33/553
(52) U.S. Cl. ..................... 436/518; 436/8; 436/172; 436/523; 436/546; 436/15; 436/164; 436/165; 436/166; 436/169; 436/800; 435/4; 435/7.1; 435/7.92; 435/7.93; 435/7.94; 435/7.95
(58) Field of Search .......................... 436/8, 172, 518, 436/523, 546, 15, 164–166, 169, 800; 435/4, 7.1, 7.92–7.95

(56) References Cited

U.S. PATENT DOCUMENTS

| | | | |
|---|---|---|---|
| 3,689,221 A | | 9/1972 | Udenfriend |
| 3,807,956 A | | 4/1974 | Morin |
| 3,917,646 A | | 11/1975 | Leimgruber et al. |
| 4,020,151 A | | 4/1977 | Bolz et al. |
| 4,023,933 A | | 5/1977 | Bradford et al. |
| 4,201,763 A | | 5/1980 | Monthony et al. |
| 4,219,337 A | | 8/1980 | Grossberg et al. |
| 4,313,734 A | | 2/1982 | Leuvering |
| 4,438,239 A | | 3/1984 | Rembaum et al. |
| 4,778,767 A | | 10/1988 | Hummelen et al. |
| 4,839,295 A | | 6/1989 | Smith |
| 5,101,020 A | | 3/1992 | Fleming .................... 534/614 |
| 5,132,439 A | | 7/1992 | Schultz et al. |
| 5,171,866 A | | 12/1992 | Khouri |
| 5,300,440 A | | 4/1994 | Alam |
| 5,571,680 A | * | 11/1996 | Chen .......................... 435/7.4 |
| 5,705,649 A | | 1/1998 | Shultz et al. |
| 5,723,346 A | * | 3/1998 | Frengen |
| 5,736,330 A | | 4/1998 | Fulton |
| 5,767,247 A | * | 6/1998 | Kaneko et al. ........... 530/388.2 |
| 5,783,673 A | | 7/1998 | Gupta |
| 5,786,461 A | | 7/1998 | Buchardt et al. |
| 5,830,912 A | * | 11/1998 | Gee et al. |
| 5,837,547 A | * | 11/1998 | Schwartz ....................... 436/10 |
| 5,846,485 A | | 12/1998 | Leland et al. |
| 6,177,277 B1 | * | 1/2001 | Soini ............................ 436/63 |

FOREIGN PATENT DOCUMENTS

| | | |
|---|---|---|
| WO | WO 97/14028 | 4/1997 |
| WO | WO 98/59233 | 12/1998 |
| WO | WO 99/19515 | 4/1999 |
| WO | WO 99/36564 | 7/1999 |
| WO | WO 99/37814 | 7/1999 |
| WO | WO 99/52708 | 10/1999 |
| WO | WO 99/57955 | 11/1999 |
| WO | WO 99/58955 | 11/1999 |
| WO | WO 99/58958 | 11/1999 |

OTHER PUBLICATIONS

Shapiro, *Practical Flow Cytometry*, Willey–Less, NY, 1995.
Fulton, et al., Clin. Chem. vol. 43, 1997: 1749–56.
PCT Written Opinion from the International Preliminary Examining Authority, United States.

* cited by examiner

*Primary Examiner*—Christopher L. Chin
*Assistant Examiner*—Pensee T. Do
(74) *Attorney, Agent, or Firm*—Gilberto M. Villacorta; Robert R. Seabold; Katten Muchin Zavis Rosenman

(57) ABSTRACT

A process, a test kit, calibration standards, and the method of preparing such standards as useful for the qualitative and/or quantitative determination of total solid phase- or microparticle-immobilized, amine-containing reactants such as proteins is provided. The operating principle of the invention is distinct from a classical immunoassay based on antibody-antigen immune interaction or from standard calorimetric proteins assays of soluble proteins and allows the detection of as low as attogram ($10^{-18}$ gm) levels of total analyte per microparticle.

18 Claims, 5 Drawing Sheets

PARTICULATE SOLID PHASE IMMOBILIZED PROTEIN QUANTITATION

RELATED APPLICATIONS

This application claims priority from U.S. Provisional Application 60/121,497, filed Feb. 24, 1999, incorporated herein by reference.

1. Field of the Invention

The invention relates to a process for the quantitation of an analyte of interest and more particularly to the quantitation of an analyte, e.g., protein, immobilized on a solid phase, e.g., microparticle, by calibrating against similarly prepared standard microparticle preparation(s) with the known amount of the reference substance. The invention also provides a kit for the quantitation, a set of standards with a reference substance bound thereto, and the method of preparing said standards. The operating principle of this novel invention is radically different from a typical immunoassay based on antibody-antigen interaction or from colorimetric protein assays.

2. Background of the Invention

The need to accurately determine the concentration of total protein has led to the development of numerous protein quantitation methods. While available protein assay methodologies are designed to quantitate total protein in solution, there is often a need to quantitate total protein immobilized on a solid phase. All solid phase, e.g., immunochemistry, applications involve a reactant that is immobilized on a surface. The reactant is usually a protein and may function as an antigen or antibody (see for example U.S. Pat. No. 4,778,767 issued to Hummelen et al.). The density to which the reactant is immobilized on the interface has a direct relationship to its function within its intended system. Therefore, having a means to quantitate the reactant per unit solid phase is critical in the optimization and control of a given solid phase coating process.

Some aqueous protein assay methodologies have been adapted to estimate total protein immobilized on a solid phase, e.g., bead surface, ELISA wells, affinity columns. These adaptations are only useful for solid phase protein quantitation if the total contributing surface area (bottom of a well in 96-well plate) is sufficient to register within the sensitivity of the assay method. The principles of such assays are disclosed in U.S. Pat. Nos. 4,020,151 and 4,201,763.

Among the most common protein assay methods are following (with sensitivity ranges indicated in parentheses): Lowry protein method (2–100 micrograms or $\mu g$), Bradford dye binding protein assay or Coomasie Brilliant Blue dye assay (1–200 $\mu g$), biuret method for protein quantitation (1–10 mg), amido Black method (2–24 $\mu g$), and Smith or bicinchoninic acid assay (BCA) for protein concentration determination (0.2–50 $\mu g$). Other protein assays are known, e.g., Folin-Ciocaulteau protein assay. The most sensitive assay (20–640 nanograms or ng) is based on a reaction of a protein with colloidal gold creating a stable color which may be read in a spectrophotometer with a filter set at 595 nanometers (nm) wavelength. Principles of some of the above methods are disclosed, for example, in U.S. Pat. Nos. 5,300,440, modified Lowry method); 4,023,933 or 4,219,337 (Bradford or Coomassie Brilliant Blue methods); 3,807,956 (Biuret method); 4,839,295 (Smith or BCA method); 4,313,734 (colloidal gold method). However, there are also known variants of protein assays, such as fluorescamin assay, wherein instead of a color a fluorescent light is produced and results can be read in a fluorescence reader or fluorometer (see for example U.S. Pat. Nos. 3,689,221 and 3,917,646). Nevertheless, the lowest detection level of the most sensitive protein assay is in the range above high nanogram levels. Nanogram herein refers to $10^{-9}$ gram. Occasionally, some of antibody-antigen-interaction-based immunoassays may provide detection sensitivity in the higher end of picogram range, but such assays are not protein assays in proper parlance. Picogram refers to $10^{-12}$ gram. Thus, to the best of this inventor's knowledge no protein assay exists that may provide sensitivity extending into femtogram ($10^{-15}$ g) or attogram ($10^{-18}$ g) ranges.

In a typical protein assay as listed above, a chemical reagent is added to a protein sample, producing a visual result, such as a color change in the sample solution. This color change is measured with a spectrophotometer or microplate reader, and compared to a standard curve in which known concentrations of protein are reacted with the detection reagent. Commonly these reagents develop a color as result of reagent reaction with peptide bonds of the analyte containing an amine or —$NH_2$ group. The amount of protein in the unknown sample can be interpolated, using its light absorbance and comparing it to the standard curve. Most commonly used standard reference proteins are bovine gamma globulin (BGG) and bovine serum albumin (BSA).

These methods have severe limitations for the measurement of total protein on particulate solid phases wherein the protein-capturing surface area is the limiting factor to produce detectable levels of color intensity. While current immunoassay systems are engineered to use less reactive surface, the ability of existing protein quantitation methods are orders of magnitude removed from being able to accurately measure the reactant concentrations typically immobilized in many particulate solid phase systems. Usually such microparticles, also referred to as microspheres, microbeads or beads, are coated with a biological reactant and often the biological reactant is a protein. In light of increasing novel applications for small particles as reactive carriers or delivery systems there is a heightened need for an innovative tool or approach to characterize and control a coating process for these solid phase systems.

The total protein present on a solid phase is often in the attogram to picogram range for many particulate solid phase (microparticle) applications. Due to this limitation it is impossible to measure by standard calorimetric methods the levels of microparticle-bound protein below nanogram levels. and therefore a considerable number of solid phase units would be necessary to attain the range of detection by these methods. The accuracy of the protein estimate becomes contingent on defining the number of solid phase units that contribute to the reaction. If the particles and protein are costly then this approach becomes impractical. Further, without the ability to measure the protein content on an individual particle, there is no means of gauging particle to particle coating variability. Consequently, one skilled in the art is not practically and completely able to assess low levels of solid phase-bound protein since no methods exist in the prior art that would combine the required microscale sensitivity and straightforward simplicity of standard protein assays.

Microscopes are devices used to examine small objects. A flow cytometer or flow analyzer is a specialized microscope designed to examine the optical properties of cells and is also useful to examine optical properties of other particle types. Flow cytometric analysis involves the steps of exposing individual fluorescently-labeled particles, as they flow in a stream of liquid, to light beam at a specific wavelength, referred to as absorption light. The fluorescent dye will then emit the light at a longer wavelength. This type of light excitation and emission phenomenon is generally known as fluorescence. Various parameters of fluorescent light, e.g., emission light spectra, an intensity of fluorescence, etc., are recorded and analyzed by a dedicated computer with an adequate software. Most commonly fluorescence intensity is expressed and directly proportional to linear or log fluorescence intensity units, occasionally referred to as fluorescence channels. Fluorescence intensity serves as an indication of relative abundance of the analyte of interest in a test sample. As a result, one skilled in the art is able to determine the presence or absence of an analyte and measure the relative amount of an analyte based on fluorescence/light emission pattern, i.e., optical signal. The fluorescent emission is made meaningful by comparing to analyte standards or reference material.

It would be an important advancement in the art to have simple means of accurately and efficiently quantitating total solid phase immobilized protein of interest especially at the concentrations and degree of precision unattainable by prior art processes.

SUMMARY OF THE INVENTION

The embodiment of the present invention entails a novel combination of separately existing chemistries and instrumentations to offer an ultrasensitive method for the quantitation of an analyte of interest such as a protein immobilized on a particulate solid phase, i.e., the surface of a microparticle, which serves as a carrier, support, or matrix. Due to amine-reactive nature of the signal label, any analyte of interest other than protein and having at least one amine group can be used in this process. As used hereinafter the term protein refers not only to a protein, but also to any substance of interest having at least one amine group. An amine can be selected from the group consisting of aliphatic amines, aromatic amines, diamines, polyamines, and substituted amines, e.g., acetamidyl, amidyl, or aminyl.

It is a further object of this invention to provide means of detecting and measuring such analytes. Analytes readily comprise most diverse classes of chemicals including proteins, peptides, prosthetic proteins, biogenic amines, various drugs with amine residues, transaminated nucleic acids, etc. Analytes also comprise fluorescent dyes having an amine group(s), e.g., phycobiliproteins, bound to a microparticle and is either labeled with another amine-reactive dye such as fluorescein isothiocyanate (FITC) or not labeled. One skilled in the art easily recognizes other similar substances like peptide nucleic acids having nucleobases attached to a polyamide backbone and containing alkylamine side chains as disclosed for example in the U.S. Pat. No. 5,786,461 and incorporated herein by way of reference.

The preferred method of making a standard microparticle preparation with a known average amount of a reference substance bound thereto comprises the steps of binding or associating a known average amount of a reference substance to a microparticle; and measuring the amount of microparticle-associated or bound reference substance by a standard calorimetric protein assay.

The preferred steps involved in this process are preferably, but not necessarily, carried out in the following sequence: immobilizing an analyte of interest on a particulate solid phase (e.g., microparticle) either by adsorption or by covalent conjugation; covalently binding to the analyte of interest a light-emitting signal molecule or signal label; comparing the intensity of the light emitted from the label to standard microparticle preparations with known amount of reference material or substance, which is labeled with the same light-emitting label under essentially same conditions, and determining the presence and/or amount of the analyte of interest. Typical standards will contain varying amounts of an immobilized reference protein extending across attogram to femtogram concentrations. For example, a series of standards ranging from 0.1 to 1000 femtograms per unit solid phase are sufficient for most common practical applications More specifically a process is provided for determining the relative average amount of at least one protein of interest, which is immobilized on each of a plurality of particulate solid phases, comprising: subjecting under substantially the same protein labeling conditions a plurality of particulate solid phases to each of which is immobilized an unknown.average amount of at least one protein of interest and a plurality of standard particulate solid phases to each of which is immobilized a known average amount of at least one reference protein, to provide protein of interest and reference protein both labeled with at least one light-emitting label; and comparing the average amount of light emitted by labels found on the standard particulate solid phases harboring the reference protein with that emitted by labels found on particulate solid phases harboring the protein of interest, to provide a relative average amount of the protein of interest immobilized on each of the particulate solid phases.

An alternative preferred method of measuring the concentration of an analyte bound to a particulate solid phase is also provided. This method consists of associating the analyte of interest with the particulate solid phase, e.g., microparticle, which has a light-emitting label embedded within or immobilized thereon. The label is chosen in such a way that it is capable of changing its light absorption and/or emission pattern as a function of the concentration of the analyte. In addition at least one and preferably more reference samples are prepared with the known amount of the reference substance bound to the solid phase. This solid phase has the same light-emitting label and the reference substance is bound to the microparticle by essentially identical procedure as the analyte. The measurement of the amount of bound analyte is then achieved by comparing the light emission characteristics or the optical signal with the light emission spectra (optical signal) of the reference sample(s).

The preferred method comprises quantifying the amount of at least one protein of interest immobilized directly or indirectly on a particulate solid phase comprising, subjecting one or more particulate solid phases, to each of which is immobilized directly or indirectly an unknown amount of at least one protein of interest, to labeling conditions effective to affix to each particulate solid phase an effective amount of a light-emitting label to provide a labeled amount of the at least one protein of interest which is proportional [sufficient to label] to the amount of the at least one protein of interest immobilized to the particulate solid phase; and elating the amount of light emitted from each particulate solid phase to the amount of the at least one protein of interest immobilized to the particulate solid phase using a standard curve. The average amount of the reference substance bound to the microparticle is in a range between about 0.01 and 1,000 femtograms per microparticle.

The preferred method of measuring the quantity of an analyte bound to a particulate solid phase, said method comprising the steps of binding an analyte with the particulate solid phase, said particulate solid phase having a fluorescent label capable of emitting a fluorescent signal embedded within said particulate solid or immobilized thereon, said label being capable of changing its fluorescence signal as a function of the concentration of the analyte; providing at least one standard microparticle preparation with a known average amount of a reference substance bound thereto, said standard microparticle preparation having the same fluorescent label as said particulate solid phase and measuring the quantity of the analyte [associated with] bound to the particulate solid phase by comparing the fluorescence signal emitted from said particulate solid phase with the fluorescence signal emitted from the standard microparticle preparation.

To achieve higher precision it is preferable that the reference substance is labeled with the light-emitting label under the same or essentially the same reaction condition as the analyte. Typically, this means that both analyte (protein) and reference substance (protein) are labeled at the same time and in the same reaction mixture. To achieve even better precision it is preferable that both analyte and reference substance are same or closely related classes of proteins. It is preferable that reference protein is the same as, similar to, analogous to, homologous to, or functionally equivalent to the protein of interest. For example if the analyte is an immunoglobulin it is preferable that the reference substance is also an immunoglobulin of the same isotype. If a single standard is available only at one known concentration then one can only make inferences about the relative amount of the analyte (protein) of interest. Better precision and absolute quantitation is possible when a plurality of standards with known amounts of reference proteins are available which permits constructing a standard curve and based on that one skilled in the art can interpolate the quantity of the analyte of interest.

The invention, based on measuring precisely the number or concentration of analyte molecules on a microparticle is useful for a wide variety of applications including but not limited to manufacturing of precision-coated microspheres, quality control, immunoassays, diagnostic procedures, therapeutic uses, affinity purification, environmental applications, recombinant DNA technology, drug and enzyme applications. The particulate solid phase based reagent is intended for use in assay systems such as radioimmunoassay (RIA), enzyme immunoassay (EIA), fluorescent immunoassay (FIA), luminescence immunoassay (LIA), calorimetric immunoassay, cytoimmunochemistry, cell sorting, agglutination, and alike. Other applications requiring the knowledge of the exact number or concentration of analyte molecules can be imagined and are readily recognized by those skilled in the art. As used hereinafter the term concentration refers interchangeably to the number, quantity, or amount of molecules of interest.

A method adapted to flow cytometry procedure is provided as a specific example although one skilled in the art will readily recognize that other technically equivalent procedures of measuring an analyte of interest are adaptable to exploit the disclosed invention. These include devices capable of measuring an emission light and selected from the group consisting of a microscope equipped with light-measuring device, a fluorometer, a spectrophotometer, a luminescence, or scintillation counter. Other equivalent means comprise visual inspection, digital (CCD) cameras, video cameras, photographic film, or the use of current instrumentation such as laser scanning devices, photodiodes, quantum counters, plate readers, epifluorescence microscopes, scanning microscopes, confocal microscopes, capillary electrophoresis detectors, a photomultiplier tube or light detector capable of detecting the presence, location, intensity, excitation and emission spectra, fluorescence polarization, fluorescence lifetime, and other physical properties of the light-emitting signal. These physically distinguishable optical features in combination with size and shape of the particle will characterize each distinct set of microparticles. Other properties such as magnetic inclusions in the body of the particle can be imagined by one skilled in the art.

Also provided is the method of preparing standard microparticle preparation carrying the known amount of immobilized protein or any other suitable reference substance, which is labeled in a manner and under conditions similar or identical to the processing of the analyte. Although the method combines known in the art procedures the final product, which is a microparticle with precisely defined amount of reference substance is uniquely distinct from any existing microparticle in the prior art and thus it is also an object of the invention. In the past the precise measurement of the reference substance was difficult to achieve, especially in ranges that are below sensitivity thresholds of prior art methods. The amount of bound reference substance can be as low as one attogram. For practical purposes the lower level can start in femtogram range and extend into microgram or higher ranges.

It should be apparent that another object of this invention is to provide a set of standard microparticles with known amounts of immobilized reference substance which would be incorporated in a kit for analyte assay. The microparticles themselves may contain additional, one or more fluorophores embedded at or inside the solid phase to help to distinguish one set of particles from another.

In accordance with the subject invention the preferred embodiment involves the solid phase immobilized protein standards useful for the invention and exhibit one or more, preferably all, of the following characteristics. The solid phase (microparticle) is highly uniform and suited for analysis in a flow analyzer (e.g., a suitably equipped flow cytometer), usually 1–20 $\mu$m in diameter, preferably 3–9 $\mu$m; has a standard reference protein associated with it; and has immobilized protein concentrations between about 0.01 and about 1000 femtograms or higher. The lower limit can be even lower and can easily extend into attogram range. The solid phase is preferably stable with respect to size and surface protein concentration in suspending media (however, for particular applications, such as sustained release particles designed for drug delivery, the stability is not critical, because the drug is intended to be gradually released). In addition; the solid phase may contain additional fluorophores or light-emitting dyes at or within the solid phase to correspond to specific subsets of the set.

An essential embodiment of the invention is a particulate solid phase to which is bound a known average amount of at least one reference protein, the known average amount ranging in value from about $10^{-9}$ to about $10^{-18}$ grams. More preferably the known average amount ranges in value from about $10^{-12}$ to about $10^{-18}$ grams. Even more preferably the known average amount ranges in value from about $10^{-14}$ to about $10^{-18}$ grams. The embodiment further comprises an average amount of at least one light-emitting label, which average amount is proportional to the known average amount of the at least one reference protein and is further characterized by one or more distinguishing properties that permit the classification of the particulate solid phase as belonging to a particular set having a predetermined known range or known average amount of the at least one reference protein. In addition it is understood that one or more distinguishing properties are defined by the size of the particulate solid phase, its shape, its color, magnetic properties, optical emission characteristics, or combinations thereof. Preferably the particulate solid phase emits light at one or more predetermined wavelengths or within predetermined ranges thereof In a preferred embodiment the microparticle immobilized analyte assay is carried out by using a kit. Such a kit is useful for determining the concentration of a protein immobilized on a particulate solid phase comprising first container containing a light-emitting label having at least one reactive functional group; and one or more second containers each containing a plurality of standard particulate solid phases harboring a known average amount of at least one reference protein. Such a kit can be minimal containing only essential proprietary component not available commercially from other sources, i.e., standards preparation. This preparation will be then processed by a practitioner in parallel with the unknown amount of analyte of interest according to the process as disclosed in detail infra. Alternatively, such a kit is essentially a complete kit containing all necessary components in one package and consisting of various buffers and reagents, light-emitting label stock, uncoated microparticles, and microparticle immobilized standards or reference substance.

These and other objects of the invention will become apparent to those of ordinary skill in the art, especially after consideration of the following detailed description of the preferred embodiments.

DETAILED DESCRIPTION OF PREFERRED EMBODIMENTS

Figure 1:
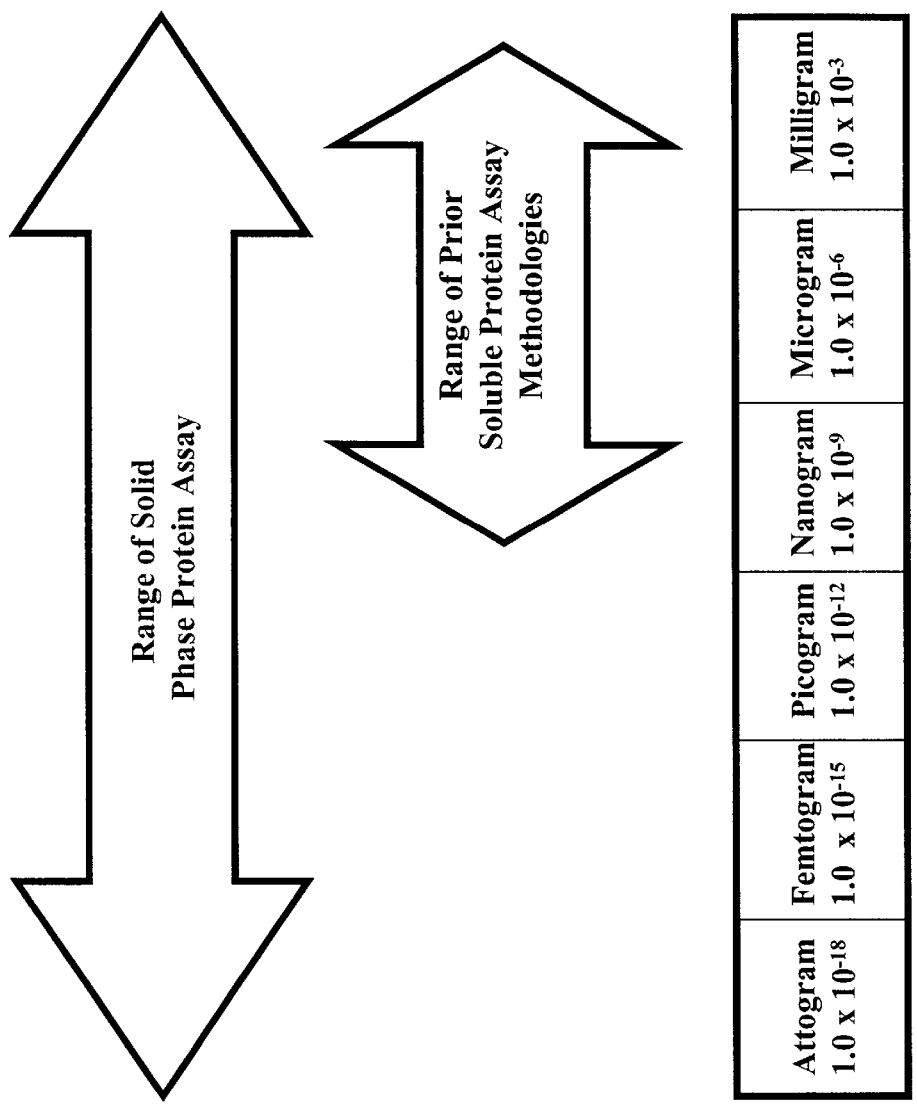
FIG. 1 illustrates the detection range of the invention and the range of prior protein assay methodologies.

In a general aspect, the invention is an analytical process whereby the total analyte immobilized on a solid phase is measured using a reporter fluorochrome bound to analyte and by calibrating against at least one or preferably a set of solid phase standards carrying a known amount of similarly labeled reference material. The process comprises the steps of: (a) providing a solid phase or solid particulate sample of the analyte (protein) obtained as a result of the coating of the microparticle; (b) binding an amine-reactive fluorochrome or light-emitting label to a solid phase immobilized protein of interest and solid phase immobilized protein standards; (c) quantitating the concentration of surface immobilized protein or analyte of interest by comparing against particulate standards carrying known amounts of surface immobilized reference material. This process also comprises the determination of the relative average amount of at least one protein of interest, which is immobilized on each of a plurality of particulate solid phases (microparticles) by subjecting under substantially the same labeling conditions a plurality of solid particulates to each of which is immobilized an unknown average amount of at least one protein of interest and a plurality of standard solid particulates to each of which is immobilized a known average amount of at least one reference protein, to provide protein of interest and reference protein both labeled with at least one light-emitting label. Following this step the average amount of light emitted by labels found on the standard solid particulates harboring the reference protein is compared with that emitted by labels found on solid particulates harboring the protein of interest, to provide a relative average amount of the protein of interest immobilized on each of the solid particulates. Under these conditions a relative but not absolute amount of the protein of reference is estimated since the standards consists of one known concentration of the reference protein. To achieve the optimal labeling a sufficient or excess amount of light-emitting label is provided under reactions conditions effective to label the protein of interest and reference protein, which are present in the reaction tube simultaneously. However, it is possible to achieve the measurement of the relative amount when solid particulates and the standard solid particulates are subjected to substantially the same labeling conditions in a separate reaction vessels. However, better estimation of the protein of interest is achieved when a series of two or more standard solid particulates is utilized in the process, in which the two or more standard solid particulates harbor different known average amounts of at least one reference protein. It is preferable that reference protein is the same as, similar to, analogous to, homologous to, or functionally equivalent to the protein of interest. As an alternative one need not to rely on amine-reactive labels bound to protein as the construction of a standard curve permitting the determination of the amount of the at least one reference protein or of the protein of interest can be based on the amount of light emitted by labels embedded within or immobilized at the surface of the standard solid particulate harboring various amounts of the reference protein(s) or that emitted by labels embedded/immobilized at the solid particulate harboring the protein of interest. This principle is based on the physical premise that the light emission pattern of solid particulates labeled light-emitting label(s) will vary as a function of the concentration of protein coating such particles. In general the known amount of the reference protein ranges from about $10^{-9}$ to about $10^{-18}$ grams, preferably from about $10^{-12}$ to about $10^{-18}$ grams, and even more preferably from about $10^{-14}$ to about $10^{-18}$ grams. These ranges are not limiting toward higher concentrations of the analyte since determining high concentration of an an analyte is not a technically challenging task.

Departing from the conventional use of soluble protein standards, the invention uses solid phase protein standards that carry known concentrations of an immobilized reference protein. It should be apparent that an object of this invention is the composition of the standard microparticle itself since no such microparticles were known in the prior art. The process by which the standards are manufactured comprises (a) immobilization of a reference protein on a particulate solid phase; (b) standardization against soluble standards using a primary protein quantitation method.

Preparation of Solid Phase Immobilized Protein Standards

The synthesis of solid phase immobilized protein standards involves the coating of uniform particulate solid phase of known surface area with various concentrations of a reference protein. The particulate solid phase used for the standards may be of any diameter from 0.1 to 100 micrometers, preferably 1–50 micrometers ($\mu$m), and more preferably 1–20 $\mu$m or microns. The shape of the particle can vary though the preferred shape is more or less spherical as it is easier to manufacture. Any other geometric shape is, however, acceptable, as this characteristic is immaterial to the scope of the invention. The potential dynamic range of the solid phase immobilized protein standards is manipulated by increasing or decreasing the size of the particle (available surface area). Therefore, for a given surface density of reference protein the total protein will increase or decrease as a function of the size of the particle. The limit to this range is a function of a particular flow cytometers ability to accommodate a given particle size.

The chemical composition of the microparticle can also vary as it can be made of any material accepted in the art, e.g., glass, cerarnics, metal, silica, resin, latex, any plastic polymeric materials comprising polyurethane or polymerizable monomers selected from a group consisting of styrene, bromostyrene, acrylic acid, acrylonitrile, acrylamide, methyl methacrylate, vinyl chloride, vinyl benzyl chloride, vinyl acetate, vinyl toluene, vinyl pyridine, vinylidene chloride, divinyl benzene, butadiene, and isoprene as long as the reference protein can be covalently linked to the surface. Covalent binding is achieved via epoxy, aldehyde, carbodiumide, or any other known suitable linking method. The reference protein is also immobilized via any tightly selected interaction with an amine or non-amine containing intermediate. Thus, protein is immobilized on the solid particulate either directly (via amine group) or indirectly (via intermediate). The microparticles are modified for covalent coupling and reacted with the soluble protein. Unbound protein is washed from the surface. While the covalent coupling method is a preferred method other methods of attachment, e.g., adsorption, hydrogen or ionic bonding are feasible and are well known in the art (see FIG. 5).

Each specific reference substance is immobilized on a distinct microparticle type that has a unique combination of size or fluorescence attributes thus allowing multiple parameters to be analyzed at the same time. This approach referred to as multiplex analysis is disclosed for example in U.S. Pat. No. 5,736,330. The technical details regarding such microparticles can be found in a technical brochure describing the Luminex system and is enclosed herein by way of reference. This permits the standards to be provided as a mixture in a single tube. A test analyte/microparticle complex is added directly to the mixture of microparticles with immobilized protein standards. This feature eliminates the need for separate reaction reservoirs. Similarly, several analyte molecules are determined simultaneously by binding them to distinct types of beads by established procedures known in the art.

A typical reference protein is employed in the formulation of the standards and these terms as used hereinafter are interchangeable. In any protein assay, the best protein to use as a standard is a purified preparation of the protein being assayed. In the absence of such an absolute reference protein, one must select another protein as a relative standard. The best relative standard to use is one, which behaves similarly to that of the protein being assayed. Any purified protein or substance, preferably with known molecular weight and/or characteristics, can be selected as a reference standard, if only a relative protein concentration is desired.

Calibration of Solid Phase Immobilized Protein Standards

The Solid Phase Immobilized Proteins Standards are calibrated against soluble counterparts and resulting units are expressed per unit of solid phase. Bovine Gamma Globulin Immobilized Standards, for example, are calibrated against standard solutions of Bovine Gamma Globulin (BGG). The protein content per unit solid phase for the Solid Phase Immobilized Standards is calibrated using a protein quantitation system based on a colorimetric response. Anywhere from $1\times10$ to $1\times10^9$, preferably from $1\times10^7$ to $5\times10^7$ particles are used to register a colorimetric response within the detection range of the reference method. The microparticles are separated from the reaction and the colorimetric reaction intensities are compared to standard solutions of Bovine Gamma Globulin. An absolute count determination of the number of microparticles in the colorimetric reactions is determined using a Coulter™ Counter. From this data, the concentration of protein per unit solid phase is calculated by dividing the amount (e.g., micrograms) of protein detected by the absolute number of solid phase units (microparticles) that contributed to the reaction.

Protein Quantitation Method Using Solid Phase Immobilized Standards

The invention preferably employs an amine-reactive light emitting compound or fluorescent dye to quantitate total protein. As used herein the terms fluorescent dye, fluorochrome, fluorophore, fluorescent or light-emitting label or tag are equivalent terms and used interchangeably. The invention, not unlike other protein quantitation methods, takes advantage of free amine groups common to all proteins. The invention differs from existing protein quantitation methodologies in that the indicator or label associates covalently (irreversibly) with the available protein at the solid phase surface. This permits separation of bound and unbound indicator through a series of wash steps and does not require that the protein be detected in the presence of unreacted indicator. Examples of such amine-reactive fluorescent dyes are well known in the art (see for a general review Shapiro "Practical Flow Cytometry" Willey-Liss, New York, 1995; and also Stryer et al., U.S. Pat. No. 5,171,866). Most common amine-reacting fluorochromes are for example green fluorescein isothiocyanate (FITC) and red tetramethylrhodamine isothiocyanate (TRITC) dyes. However, any other convenient fluorescent dye can be used either by reacting directly with amine groups on analyte molecules or through cross-linking or linking process having an intermediate reactant molecule such as succinimidyl ester between dye and analyte. Molecules like succinimidyl ester are termed cross-linking reagents or linkers. One skilled in the art would know general procedures and will be able to select an appropriate fluorochrome for reaction purpose. Such dyes can be selected for example from the following list: 3-Hydroxypyrene 5,8,10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy Fl, BOPRO 1,Brilliant Sulphoflavin FF, Calcein Blue, Calcium Green, Calcofluor RW Solution, Calcofluor White, Calcophor White ABT Solution, Calcophor White Standard Solution, Cascade Blue, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulfonic Acid), Dansa (Diamino Naphthyl Sulfonic Acid), Dansyl NH-CH3 in water, DAPI, Diamino Phenyl Oxydiazole (DAO), Dimethylamino-5-Sulfonic acid, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258 (bound to DNA), Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin E8G, Oregon Green, Pacific Blue, Pararosaniline (Feulgen), Phorwite AR Solution, Phorwite BKL, Phorwite Rev, Phorwite RPA, Phosphine 3R, Phycoerythrin R, Pontochrome Blue Black, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulphO Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof. Other classes of dyes known as triphenylmethane dyes (and, more specifically, rosaniline dyes), acid blue 25 dyes, dansyl dyes, fluorescein dyes, or 2-methoxy-2,4-diphenyl-3(2H)-furanone ("MDPF") dyes are equally suitable.

In yet another embodiment of the invention a luminescent label can be used instead of a fluorescent label. In this situation light is emitted from a donor molecule such as luciferin as a result of a redox reaction catalyzed by the enzyme luciferase. Generation of chemiluminescence can be also provided upon reaction of amines or an amine moiety with 2,2-bipyridine ruthinium, 1-amino-3-anthryl-(9)-propane, or by other means known in the art as disclosed for example in the U.S. Pat. No. 5,846,485.

Thus, the term light-emitting label as used hereinafter, in general, refers to any label or indicator, which emits fluorescent, luminiscent, evanescent light, or chemoluminescent light.

Light-emitting label are preferably added in an amount sufficient to saturate the analyte molecule, e.g., in a range from 1 to 1000 fold and more preferably from 2–100 or 20–50 fold the final concentration of an analyte bound to the microparticle. Light in the present context refers to a light that is detected by a flow cytometer or any other light detecting device mentioned above. Such a light will normally be a light in a visible wavelength range but for particular purposes can be any emitted photons at lower or higher energies.

Due to amine-reactive nature of said label any analyte containing such groups are reliably measured. Amino refers to moieties including a nitrogen atom bonded to 2 hydrogen atoms, alkyl moieties, or any combination thereof. Amido refers to moieties including a carbon atom double bonded to an oxygen atom and single bonded to an amino moiety. Nitrile refers to moieties including a carbon atom triple bonded to a nitrogen atom. Alkoxy refers to a moiety including an alkyl moiety single bonded to an oxygen atom. Aryl refers to single or multiple phenyl or substituted phenyl, e.g., benzene, naphthalene, anthracene, biphenyl, and the like. A linking moiety can be used to attach the dye to a nucleotide, nucleoside or oligonucleotide. Examples of linking moieties include isothiocyanate, sulfonyl chloride, 4,6-dichlorotriazinylamine, succinimidyl ester, or other active carboxylate whenever the complementary functionality is amine. Amine-reactive finctional groups include activated carboxylic esters, isocyanates, glutaraldehydes, isothiocyanates, sulfonyl halides, and dichlorotriazenes see Molecular Probes catalog (Eugene, OR), N-hydroxysuccinimide esters, pentafluorophenyl esters, tetrafluorophenyl esters, and p-nitrophenyl esters, ethylene glycobis(succinimidylsuccinate) (EGS), disuccinimidyl tartarate (DST) and sulfo-DST, bis[2-(succinimidyloxycarbonyloxy)ethyl]sulfone (BSOCOES) and sulfo-BSOCOES. Numerous commercial cross-linking reagents exist which can serve as linkers (e.g., see Pierce Cross-linkers, Pierce Chemical Co., Rockford, Ill.). Among these are homobifinctional amine-reactive cross-linking reagents which are exemplified by homobifinctional imidoesters and N-hydroxysuccinimidyl (NHS) esters. There also exist heterobifunctional cross-linking reagents possess two or more different reactive groups that allows for sequential reactions. Imidoesters react rapidly with amines at alkaline pH. NHS-esters give stable products when reacted with primary or secondary amines. Maleimides, alkyl and aryl halides, alpha-haloacyls and pyridyl disulfides are thiol reactive. Maleimides are specific for thiol (sulfhydryl) groups in the pH range of 6.5 to 7.5, and at alkaline pH can become amine reactive. The thioether linkage is stable under physiological conditions. Alpha-haloacetyl cross-linking reagents contain the iodoacetyl group and are reactive towards sulffiiydryls. Imidazoles can react with the iodoacetyl moiety, but the reaction is very slow. Pyridyl disulfides react with thiol groups to form a disulfide bond. to Carbodiimides couple carboxyls to primary amines of hydrazides which give rises to the formation of an acyl-hydrazine bond. The arylazides are photoaffinity reagents which are chemically inert until exposed to UV or visible light. When such compounds are photolyzed at 250–460 nm, a reactive aryl nitrene is formed. The reactive aryl nitrene is relatively non-specific. Glyoxals are reactive towards guanidinyl portion of arginine. Crosslinking agent is selected from ethylene glycol dimethacrylate, divinyl benzene, trimethylol propane trimethacrylate, N,N'methylene-bis-acrylamide, aryl azides, fluorinated aryl azides, and benzophenones like iodoacetamide or maleimide derivatives of benzophenone (BPIA and BPM).

Some proteins in addition to amino acids may contain nonprotein moiety, called prosthetic group, which is attached by covalent, heteropolar, or co-ordinate linkage. Proteins containing prosthetic groups such as carbohydrates, lipids, nucleic acids, metals, chromogens, heme groups and phosphate residues are accordingly called as glycoproteins, proteoglycans, lipoproteins, nucleoproteins, metalloproteins, chromoproteins, hemoproteins, and phosphoproteins. The analytes of interest may also include not only prosthetic proteins but also natural and synthetic peptides, amino acid derivatives, blocked amino acids, as well as amine containing molecules such as cyanidins, biogenic amines such as ethanolamines, polymethylene diamines, polyamines, imidazolylalkylamines, phenylalkylamines, catecholamines, indolylalkylamines, betaines, or any other natural or synthetic derivatives of amino acids. These may further include diacids, hydrazines, aliphatic or aromatic amines. Among classes of biogenic amines there are many biologically important substances, e.g., choline, acetylcholine, muscarine, putrescine, cadaverine, spermine, histamine, mescaline, tyramine, hordenine, adrenaline, noradrenaline, dopamine, tryptamine, serotonin, carnitive, etc. These compounds are further labeled with light-emitting dyes or they do not have to be labeled with an extra dye since some can autofluoresce, e.g., histamine. In addition, to above-named analytes other substances with amine groups can be used in the invented process, e.g., drugs such as antithrombotic diamines or substituted phosphoethanolamines or aminonucleosides with anti-cancer properties. These may also include fumigalin and suramin, which possess anti-tumor activity. Various aminosterols such as squalamine and other similar therapeutically useful compounds recovered from extracts of shark liver can be imagined as well. Similarly, one can easily imagine amine group containing antibiotics such as aminocyclitol antibiotic. Transaminated nucleic acids having one or more amine residues can also serve as analytes of interest. Primary aliphatic amine handles can be readily introduced onto synthetic oligonucleotides with phosphoramidites such as 6-monomethoxytritylhexylcyanoethyl-N,N-diisopropyl phosphoramidite (Glenn Research, Sterling, Va.). Preferably, the nucleic acid polymer is activated prior to be contacted with a dye. This can be conveniently accomplished by combining amine-functionalized nucleic acid polymer with a multi-functional amine-reactive chemical such as trichlorotriazine. When the nucleic acid polymer contains a 5'-amine group, that 5'-amine can be reacted with trichlorotriazine, also known as cyanuric chloride. Preferred nucleic acid polymers are "amine-modified" in that they have been modified to contain a primary amine at the 5'-end of the nucleic acid polymer, preferably with one or more methylene (—CH2—) groups disposed between the primary amine and the nucleic acid portion of the nucleic acid polymer. Six is a preferred number of methylene groups. Amine-modified nucleic acid polymers are preferred because they can be covalently coupled to a solid support through the 5'-amine group. PCR products can be arrayed using 5'-hexylamine modified PCR primers. Nucleic acid duplexes can be arrayed after the introduction of amines by nick translation using aminoallyl-dUTP (Sigma, St. Louis, Mo.). Amines can be introduced into nucleic acids by polymerases such as terminal transferase with amino allyl-dUTP or by ligation of short amine-containing nucleic acid polymers onto nucleic acids by ligases.

Without limiting to these examples, one skilled in the art can imagine any other radicals as useful in this invention including, but not limited to, alkyl, alkenyl, alkynyl, cycloalkyl, aryl-fused cycloalkyl, cycloalkenyl, aryl, aralkyl, aryl-substituted alkenyl or alkynyl, cycloalkyl-substituted alkyl, cycloalkenyl-substituted cycloalkyl, biaryl, alkoxy, alkenoxy, alkynoxy, aralkoxy, aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarbonyl-substituted alkyl, heterocyclyl, heterocyclyl-substituted alkyl, heterocyclyl-substituted amino, carboxy-alkyl substituted aralkyl, oxocarbocyclyl-fused aryl and heterocyclylalkyl; cycloalkenyl, aryl-substituted alkyl and, aralkyl, hydroxy-substituted alkyl, alkoxy-substituted alkyl, aralkoxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, hydrocarbylacylarnino-substituted alkyl, heterocyclylacylamino-substituted alkyl, hydrocarbyl-substituted-heterocyclylacylamino-substituted alkyl, alkylsulfonylamino-substituted alkyl, arylsulfonylamino-substituted alkyl, morpholino-alkyl, thiomorpholino-alkyl, morpholino carbonyl-substituted alkyl, thiomorpholinocarbonyl-substituted alkyl, [N-(alkyl, alkenyl or alkynyl)- or N,N-[dialkyl, dialkenyl, dialkynyl or (alkyl, alkenyl)-amino]carbonyl-substituted alkyl, heterocyclylaminocarbonyl, heterocylylylalkyleneaminocarbonyl, heterocyclylaminocarbonyl-substituted alkyl, heterocylylalkyleneaminocarbonyl-substituted alkyl, N,N-[dialkyl]alkyleneaminocarbonyl, N,N-[dialkyl]alkyleneaminocarbonyl-substituted alkyl, alkyl-substituted heterocyclylcarbonyl, alkyl-substituted heterocyclylcarbonyl-alkyl, carboxyl-substituted alkyl, dialkylamino-substituted acylaminoalkyl and amino acid side chains selected from arginine, asparagine, glutamine, S-methyl cysteine, methionine and corresponding sulfoxide and sulfone derivatives thereof, glycjne, leucine, isoleucine, allo-isoleucine, tert-leucine, norleucine, phenylalanine, tyrosine, tryptophan, proline, alanine, omithine, histidine, glutamine, valine, threonine, serine, aspartic acid, beta-cyanoalanine, and allothreonine; alynyl and heterocyclylcarbonyl, aminocarbonyl, amido, mono- or dialkylaminocarbonyl, mono- or diarylaminocarbonyl, alkylarylarninocarbonyl, diarylaminocarbonyl, mono- or diacylaminocarbonyl, aromatic or aliphatic acyl, alkyl optionally substituted by substituents selected from amino, carboxy, hydroxy, mercapto, mono- or dialkylamino, mono- or diarylamino, alkylarylamino, diarylamino, mono- or diacylamino, alkoxy, alkenoxy, aryloxy, thioalkoxy, thioalkenoxy, thioalkynoxy, thioaryloxy and heterocyclyl.

This process could be useful for flow cytometry calibration purposes wherein fluorescent dyes having an amine group(s), e.g., phycobiliproteins, serving as an analyte of interest is bound to a microparticle and said dye is either labeled with another amine-reactive dye such as FITC or not labeled. Examples of such dyes and their conjugates can be found for example in U.S. Pat. No. 5,783,673, incorporated herein by reference.

Numerous other categories of applications can be imagined involving an amine-containing substance imrmobilized on a solid phase. The major application which can be readily seen is application in various immunoassays and usually involving antibody or antigen immobilized on solid phase, including immunodiagnostic and agglutination tests. Listed below are representative examples wherein such potential exists: Human clinical and therapeutic application may include antibiotics/antimicrobial drugs such as gentarnicin, tobramycin, amikacin, penicillin, cephalosporin, blasticidin S, viomycin, sulfa drugs, kanamycin, netilmicin, streptomycin, and vancomycin. Drugs of abuse such as opiates, barbiturates, amphetamines, methadone, cocaine, benzodiazepines, propoxyphene, phencyclidine (PCP), cannabinoids (THC), or lysergic acid diethylamide (LSD). Antiepileptic drugs such as phenytoin, phenobarbital, carbamazepine, primidone, ethosuximide, or valproic acid. Antiasthmatic drugs such as theophylline. Cardioactive drugs such as digoxin, digitoxin, lidocaine, procainamide, N-acetylprocainamide, quinidine, propranolol, diisopyramide, or flecainide. Chemotherapeutic drugs such as methotrexate. Hormones such as testosterone, estradiol, estrogens, progesterone, cortisol, thyroxine, insulin, human placental lactogen (HPL), thyroid-stimulating hormone (TSH), follicle-stimulating hormone (FSH), luteinizing hormone (LH), or human chorionic gonadotropin (hCG). Immunosuppressants such as cyclosporin A (CsA), cyclosporin G (CsG, OG37-325), or FK506 (tacrolimus). Serum proteins such as albumin, $\alpha_1$-acid glycoprotein (orosomucoid), serum amyloid P component (SAP), serum retinol binding protein, thyroxine binding globulin (TBG), $\alpha_1$-antitrypsin, $\alpha_2$-macroglobulin, anti-DNA antibodies, antithrombin III, apolipoproteins AI and AII, apolipoprotein BI, prealbumin (transthyretin), C1 inactivator, C3 protein, ceruloplasmin, fibronectin, haptoglobin, hemopexin, somatotropin, transferrin, immune complexes, immunoglobulin A, immunoglobulin E, immunoglobulin G and its subclasses, immunoglobulin M, immunoglobulin light chains, rheumatoid factor, $\beta_1$-microglobulin, Cl-esterase inhibitor, C4-protein, or C-reactive protein. Various tumor markers, e.g., $\alpha$-Fetoprotein, carcinoembryonic antigen (CEA), human chorionic gonadotropin (hCG), $\beta$-hCG, pregnancy-specific protein (SP1), placenta-specific protein (PPS), placental alkaline phosphatase (Regan type), isoferritins, tissue polypeptide antigen, Tennessee antigen, pancreatic oncofetal antigen (POA, OPA), prostatic acid phosphatase, carbohydrate antigen 19-9 (sialyl Lewis), carbohydrate antigen 50, cancer antigen 125, cancer antigen 15-3, fecal occult blood, $\beta_2$-macroglobulin, neuron specific enolase, or squamous cell carcinoma antigen. Many allergens such as total serum IgE, allergen-specific IgEs, pollen allergens, epithelial allergens, house dust, occupational dusts, molds, foods, chemicals, or drugs. Similar applications can be imagined in parasitic and infectious diseases and/or causal organisms—human immunodeficiency virus (HIV), hepatitis, influenza, herpes, Toxoplasma, rubella, cytomegalovirus (CMV), adenovirus, coxsackieviruses, arbovirus, malaria, schistosomiasis, trypanosomes, Trichinella, *Chlamydia trachomatis, Neisseria gonorrhoeae*, amoebiasis, typhoid, leprosy, or tuberculosis. In autoimmune diseases, e.g., rheumatoid factor (RF), polyarthritis, juvenile chronic polyarthritis, ankylozing spondylitis, Reiter's syndrome, antinuclear antibodies (ANA), anti-DNA antibodies, antihistone antibodies, acetylcholine receptor antibodies, antierythrocyte antibodies, antiplatelet antibodies, or thyroglobulin antibodies. In quantitating bacterial, mycoplasmal, and fungal antigens and antibodies like Salmonella O antigens, *Vibrio cholerae* O antigens and exotoxins, *Escherichia coli* O and K antigens, *Haemophilus influenzae* polysaccharide, *Treponema pallidum, Brucella* and *Yersinia enterocolitica* O antigens, *Francisella rularensis* O antigen, *Candida albicans* and *Aspergillus fumigalus* cell wall and cytoplasmic antigens, Streptococcus M protein, Mycoplasma, Rickettsia, Chlamydia, *Clostridium tetanus* exotoxin, or *Corynebacterium diphtheria* exotoxin. Equally important application can be found in agricultural field. For example, in measuring plant hormones like cytokinins, gibberellins, indole-3-acetic acid, or abscisic acid. In detecting spoilage microorganisms—Erwinia spp., Fusarium spp., *Humicola lanuginosa, Legionella pneumophila, Ophiostoma ulmi, Phylophthora megasperma, Pseudocercosporella herpotrichoids. Pseudomonas syringae, Rhizoctonia solani, Xanthomonas campestris*. In identifying plant viral agents—Beet necrotic yellow vein virus, cauliflower mosaic virus, citrus tristeza virus, cucumber mosaic virus, elongated potato virus, isometric plant viruses, pea seedborne mosaic virus, potyviruses, soybean mosaic viruses, or zucchini yellow mosaic virus. One can find widespread application in food industry by measuring for example bacterial toxins—*Clostridium botulinum* neurotoxins A, B, E, F, and G; *Staphylococcus aureus*, or enterotoxins A, B, C, D, and E. Food safety concerns can be equally addressed by detecting mycotoxins, aflatoxins $B_1$, BC, $B_1$diol, $M_1$ and $Q_1$-, ochratoxin,T-2 toxin, 3'-OH-T-2 toxin, T-2 tetraoltetraacetate, HT-2 toxin, group A trichothecencs, rotidin A, zearalenone, rubratoxin B, sterigmatocystin, deoxyverrucarol, or deoxynivalenol. Also in category of food safety one can look for pathogenic microorganisms such as Salmonella, *Listeria monocytogenes, Escherichia coli*, Vibrio spp., *Yersinia enterocolitica*, or *Campylobacter jejuni*. Miscellaneous health issues such as mushroom poisoning, algal and seafood toxins, or potato glycoalkaloids can be addressed. Various food enzymes such as $\alpha$-mylase, $\beta$-amylase, catalase inhibitor, chymotrypsin, debranching enzyme, lipase, malate dehydrogenase, papain, pepsin, polyphenoloxidase, proteolytic enzymes, and trypsin can be successfully measured. In addition, interspecies meat and adulterant identification can be deployed using the invention, e.g., beef, sheep, pig, goat, horse, meat products, sausages, processed meats. Amine containing food additives such as biocides, water treatment chemicals, plastic additives, and petroleum product additives can be also detected as well. Similarly, this invention can find application in veterinary practice, e.g., in livestock diseases and/or causal organisms—*Toxoplasma gondii, Brucella abortus, Stephanauras dentatus, Mycoplasma bovis, Leptospira interrogans, Trichinella spiralis, Mycobacterium paratuberculosis*, bovine rhinotracheitis, maedi-visna virus, swine fever virus, coronavirus, Aujeszky s disease, swine vesicular disease, enzootic bovine leukemia, foot and mouth disease, avian PMV1, rotavirus, or sheep lungworm disease. Other veterinary uses can be imagined such as detection of anabolic agents, i.e.,17$\beta$-Estradiol, estrone, testosterone, 17-methyltestosterone, progesterone, trenbolone, diethylstilbestrol, hexoestrol, zeronal, or therapeutic agents, i.e., cephalexin, chloramphenicol, colistin, gentamicin, hydromycin B, monensin, sulfonamides, penicillins, or cephalosporins.

Without limiting to above examples one can easily adapt the invention to measure immobilized reactants for environmental testing applications aimed at identifying and measuring pesticides and their aminated metabolites including but not limited to aldrin, alachlor, atrazine, BAY SIR 8514, S-bioallethrin, chlorosulfuron, cyanazine, 2,4-D, DDT, dichlorfop-methyl, dieldrin, diflubenzuron, endosulfon, iprodione, kepone, maleic hydrazide, metalaxyl, oxfendazole, parathion, paraoxon, paraquat, pentachlorophenol, 2,4,5-T, terbutryn, triadimefon, warfarin. Environmental pollutants of concern, e.g., polychlorinated biphenyls (PCBs), polybrominated biphenyls (PBBs), polynuclear aromatic hydrocarbons (PARs), nitroaromatics, cyclic ketones, BTEX (benzene, toluene, ethyl benzene, and xylene), nitrosamines, haloalkanes, dioxins, dibenzofurans, or TNT can be imagined as being quantifiable by instant method.

The compositions of the invention in conjunction with internal standards are equally suitable for detecting and correcting immunoassay-interfering factors such as hook effect (excess of an antigen in a sample), presence of interfering autoantibodies (e.g., rheumatoid factor) or assay-interfering proteins or substances (e.g., bilirubin, hemoglobin, lipids), failure to add sample, etc.

Other uses may include the field of combinatorial chemistry, e.g., screening of combinatorial libraries for drug discovery that could include any receptor-ligand, protein subunit interactions, drugs, nucleic acid binding assays, or enzymatic assays. Applicability of the process can be imagined in receptor-ligan dassays, i.e., receptor or ligand immobilized on solid phase, e.g. characterization of receptor-ligand interactions such as hormone binding events; in protein subunit interactions—protein subunit immobilized on solid phase, e.g., characterization of protein subunit associations; in nucleic acid binding assays, e.g., antibody to specific nucleic acid sequence or nucleic acid binding protein immobilized on solid phase, e.g., transcriptional factor binding; in enzymatic assays—enzyme or proteinaceous sublunit on solid phase, e.g., activation or inactivation of proenzymes such as complement or clotting factors; in pre-coated (activated) particles—amine-containing capturing component immobilized on solid phase for easy immobilization of other reactants, e.g., protein G, protein A, avidin, streptavidin, neutravidin; and also in affinity purification columns—proteinaceous capturing component immobilized on solid phase (usually beads) for immobilization of target molecules, e.g., protein G, antigen-antibody. Thus, a variety of applications for the process can be imagined and as disclosed herein these examples are not in any way limiting but serve only for the purpose to illustrate these and many other possible applications requiring quantitative data.

The invention differs from existing methodologies in that the all components in this assay are bound in a sequential manner covalently or irreversibly at the microparticle surface. This feature is distinct from any prior art approaches to protein quantitation, which inveaiably involves non-covalent associations, viz., as in the Lowry protein method, Bradford dye binding protein assay, amido Black method, or colloidal gold method. This novel approach permits not only the enhancement of the detection threshold by several orders of magnitude, but also an efficient separation of bound and unbound reagents through a series of wash steps and thus reducing the background noise.

The method involves an analyte of interest, e.g., protein immobilized on the surface of a microparticle and similarly immobilized standards or reference proteins. The microparticle can be of any size ranging from 0.01 to 100 micrometers ($\mu$m), preferably 0.1–50 $\mu$m, more preferably 1–20 $\mu$m, and even more preferably 3–9 $\mu$m. However, one skilled in the art will recognize that for certain application needs microparticle sizes can be much larger, up to 1,000 $\mu$m. For example, antibody-coated beads are packed in affinity purification columns through which a biological fluid, e.g., cell culture supernatant containing an antigen of interest is passed. This antigen will be captured by the antibody immobilized on such beads and thus separated from the rest of fluid. To manufacture such antibody-coated beads one may need to know the amount of antibody per bead and adjust the number of antibodies to desired optimal concentration. Similar approach can be imagined by using beads coated with protein A or G or by using beads coated with avidin/streptavidin/neutravidin which would capture immunoglobulin or biotinylated products of interest. Large beads are also used in agglutination assays as well.

It is preferable that within one defined set of particles the size of solid phase unit is uniform and consistent from one particle to another. The shape of microparticle can vary, though the preferred shape is spherical. The surface of particles can be smooth, relatively smooth or porous. The physical density of microparticles can be also variable and will depend on particular needs required by the assay. The microparticles can be hydrophobic or hydrophilic by nature.

The chemical composition of the microparticle can also vary as it can be made of any material accepted in the art, e.g., glass, ceramics, metal, silica, resin, virion, cell, latex, any plastic polymeric materials comprising polyurethane or polymerizable monomers selected from a group consisting of styrene, bromostyrene, acrylic acid, acrylonitrile, acrylamide, methyl methacrylate, vinyl chloride, vinyl benzyl chloride, vinyl acetate, vinyl toluene, vinyl pyridine, vinylidene chloride, divinyl benzene, butadiene, and isoprene as long as the analyte of interest can be covalently linked or adsorbed to it. In other applications, such as sustained drug delivery for therapeutic purposes, beads or drug vehicles may contain a drug of interest not only on the surface but dispersed throughout the body of the particle and the particle itself is made of biodegradable material. Nevertheless, one may deduce the amount of the drug by using the invention.

Covalent binding of the analyte to a microparticle can be achieved via epoxy, aldehyde, carbodiimide, or any other known suitable linking method. Carbodiimides which can be employed are N,N-dicyclohexylcarbodiimide, 1-ethyl-3(3-dimethyl aminopropyl)carbodiimide hydrochloride and 1-cyclohexyl-3-(2-morpholinyl-(4)-ethylcarbodiimide) methyl-p-toluene sulfonate.

A crosslinking agent, such as divinyl benzene may be also present on the surface of these microparticles. Other crosslinking or bifunctional coupling agents which can be utilized are compounds having two or more of the following reactive groups: azo, sulfonic acid, fluoro groups activated by nitro groups, azide, imine and reactive chloro groups connected to a ring having proper resonance structure. These reactive groups are capable of reacting with the primary amino, sulfylhydryl, carboxylic, hydroxyl and phenolic groups in the substances that constitute the majority of the solid phase polymeric carriers disclosed herein as suitable for the preparation of the particles as well as the bioactive protein or analyte to be coupled thereto. Representative of such other coupling agents are bis-diazobenzidine, disulfonic acid, tetraazo-p-phenylenediamine, difluorodinitrobenzene, difluorodinitrophenylsulfone, a carbodiimide, toluene diisocyanate, cyanuric chloride and dichlorotriazine.

These coupling agents may or may not have additional surface groups, such as carboxylates, esters, alcohols, carbamides, amines, sulfur oxides, nitrogen oxides, or halides. The functionality of the microspheres surface groups gives the microparticles their coupling characteristics, which may be useful for specific applications. Protocols concerning some of such methods can be found for example in U.S. Pat. No. 4,438,239 as incorporated herein by reference. The amount of coupling reagent utilized in the process of this invention will depend upon the particular analyte to be coupled and on the pH of the coupling solution. The amount can be readily determined by those skilled in the art but typically will be an amount sufficient to link or cross-link the carrier and analyte or analyte and the label reagent.

Figure 5:
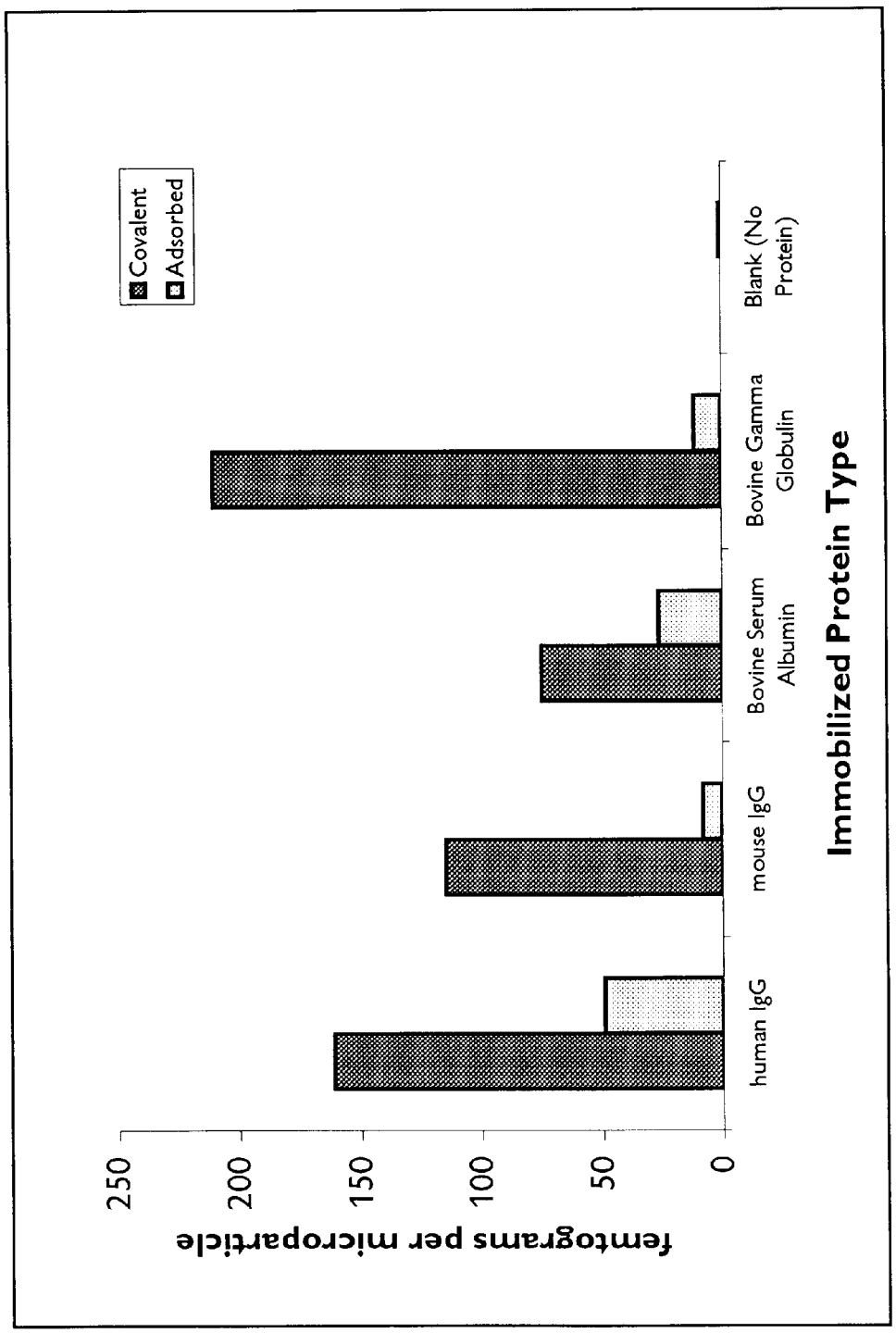
FIG. 5 presents series of tests wherein various proteins, that are bound either covalently or by adsorption, could be detected on solid phase such as the surface of microspheres as femtograms/microparticle amounts.

Another way of bonding is by adsorption (FIG. 5). Adsorption of the analyte can be passive by simply incubating for a sufficient period of time or active by employing established physical or chemical methods known in the art, e.g., by varying temperature or pH of the incubation reaction. Microparticles as carriers can be further labeled with an additional fluorochrome or a set of fluorescent dyes as for example in Luminex system approach (Fulton et al. Clin Chem 43:1749–1756, 1997). This would allow performing multiplexed analysis of up to 64 color spectra parameters.

For example, one set of beads may contain on its surface 15% red and 85% orange fluorescent dyes which would allow to distinguish it from another set of beads displaying 50% red and 50% orange fluorescence. Different multicolor sets of beads may be used to conjugate with specific protein standards allowing to distinguish varying concentration of reference substance on each set as a function of beads light spectra. Detailed description of this methodology and methods of detection by flow cytometry can be found in commonly-owned published PCT applications WO 99/58958, WO 99/58955, WO 99/57955, WO 99/52708, WO 99/37814, WO 99/36564, WO 99/19515, WO 97/14028, and WO 98/59233, incorporated herein by reference. This plurality of sets or subsets can be also discriminated by different shape or size of microparticles. The size of the microparticle can be measured in practically any flow cytometry apparatus by so-called forward or small-angle scatter light. The shape of the particle can be also determined, e.g., by high resolution slit-scanning method. The physical density of the particles can also be variable.

Unlike instrumentation required for other protein assay methodologies, the invention has adapted principles of flow cytometry as a principal mode of analysis. Although, as mentioned hereinabove, other apparatuses can be used instead of a flow cytometer. The flow cytometer employs a laser to illuminate the particles as they flow in a single file along the axis of the viewing chamber. Scattered and fluorescent light is collated with each microparticle event that serves to identify and measure a fluorescent intensity related to the amount of bound indicator present. Since hundreds of replicates for each microparticle population are collected the data is reported as a mean fluorescent intensity. Equally important, is the coefficient of variation, which is the ratio of the standard deviation to the mean intensity of the fluorescence. The coefficient of variation provides a measure of the coating homology between microparticles. A smaller coefficient of variation would indicate more consistent inter-microsphere coating homology.

In a preferred embodiment the Microparticle Immobilized Protein Assay is provided as a kit consisting of Reaction Buffer, Wash Buffer, Amine-Reactive Light Emitting Label, Fluorescent Label Stock, and Solid Phase Immobilized Protein Standards. During a given protein immobilization process a small sample of the subject solid phase is removed after unbound protein is washed free from the surface and prior to the addition of blocking agents. The sample is added directly to the Solid Phase Immobilized Protein Standards. The assay is not dependent on the exact number of microparticles in the reaction, so the amount of microparticles added is not critical. The Fluorescent Label is added to the reaction and incubated. After incubation the unbound indicator is washed free from the microparticles. Reactions are analyzed in a flow cytometer where the subject microparticles and the standards are segregated using gating techniques and fluorescent intensities related to amount of detected protein is reported.

A standard curve is prepared by plotting the fluorescent intensities of the Standards against their lot specific protein concentrations. Using the standard curve, protein concentrations for the subject microparticle preparation(s) may be interpolated. The resulting protein concentration would be per unit solid phase.

The following Examples are presented to illustrate the advantages of the present invention and to assist one of ordinary skill in making and using the same. These Examples are not intended in any way to otherwise limit the scope of the disclosure or the protection granted by Letters Patent hereon.

EXAMPLES

Procedure for microparticle immobilized protein using flow cytometry materials and reagents Microparticle-Bound Bovine Gamma Globulin Protein Assay Multiplex Standards; Amine-reactive light-emitting label—Fluorescein isothiocyanate; Reaction Buffer—0.1 M Sodium Bicarbonate, pH 8.2–9.5; Wash Buffer—Phosphate Buffered Saline (PBS), pH 7.47 with 0.05% Tween 20; and Microtiter plate with filter bottom, 96 well.

Procedure

After harvesting coupled microspheres in PBS and prior to the blocking step remove approximately 1.0E+4 to 5.0E+4 microspheres in duplicate from each microsphere preparation and dispense into filter bottom microtiter well.

Microparticle-Bound BGG Multiplex Standards

Remove Microparticle-Bound BGG Multiplex Standards from refrigerated storage and allow to reach ambient temperature (5 min). Vortex Standards for 10–12 seconds. Avoid over mixing. Dispense 50 µl of the Standards into each filter bottom microtiter well containing test article. Position plate on vacuum manifold and apply low vacuum until microtiter well is drained.

Labeling with light-emitting or fluorescent label

Rehydrate Protein Reactive Label, e.g., fluorescein isothiocyanate, in Reaction Buffer at 100 µg/ml to make Working Label Reagent. Add 100 µl of Working Label Reagent into one of each duplicate well containing standards and test articles. Add 100 µl of Reaction Buffer without the Label into remaining duplicate wells containing standards and test articles (background controls). Incubate with shaking for 60 min at room temperature in the dark. Position the plate on vacuum manifold and apply low vacuum to remove free Label. Wash wells by multichannel addition of 200 µl of Wash Buffer and apply vacuum to remove wash solution. Repeat this step twice. Perform final resuspension by multichannel addition of 200 µl Wash Buffer. Acquire Relative Linear Mean Fluorescent Values for at least 100 singlet gated events per microparticle type.

Calculations

Calculate Net Relative Linear Mean Fluorescent Values by subtracting the background controls from their respective standard and test article series. Using a curve fitting software program, prepare a curve fit for the standards by plotting the Net Relative Linear Mean Fluorescent Values vs. the femtograms of protein/microparticle specified for the Standards. Interpolate the femtograms of protein/microparticle detected for each test article. Calculate the molecules of protein per microsphere according to the formula shown below.

Molecules of Protein/Particle = (femtograms of protein/particle) / ((MW of protein) / (6.022E + 23) * (1.0E + 15))

Figure 3:
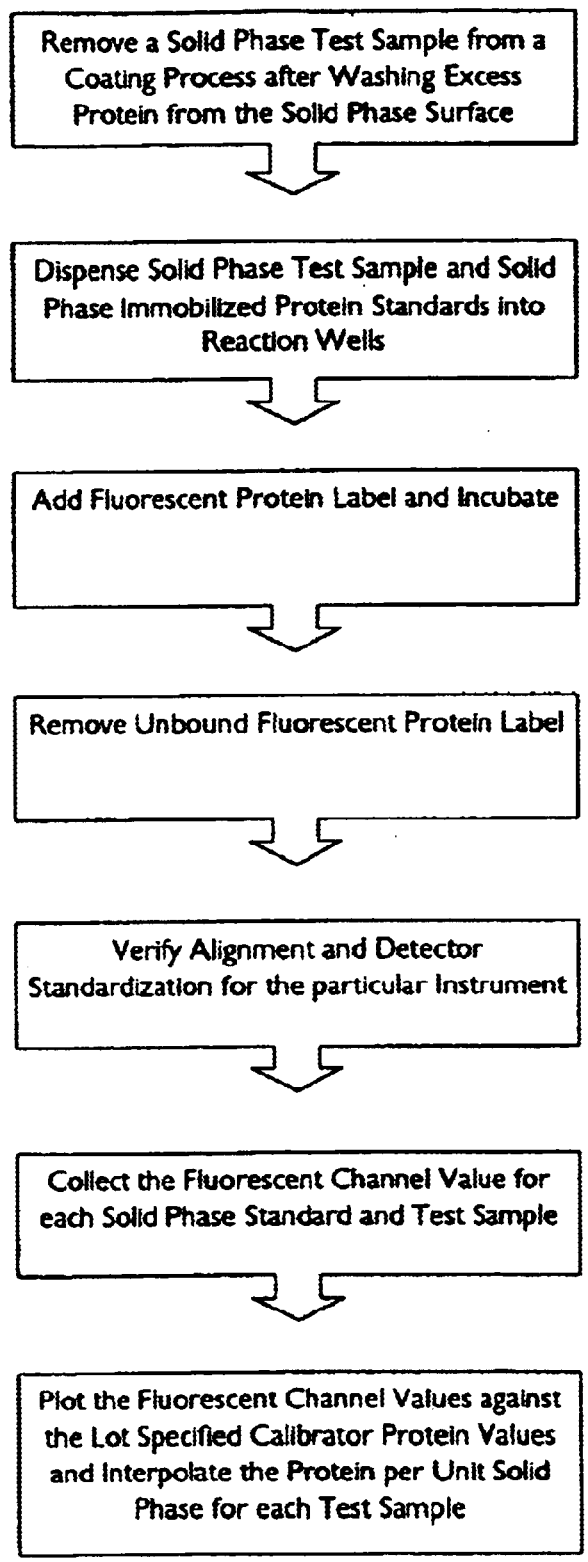
FIG. 3 shows a flow chart with sequential steps for determining by flow cytometry the quantity of the analyte of interest in relation to standard preparations with known amount of reference substance.
Figure 4:
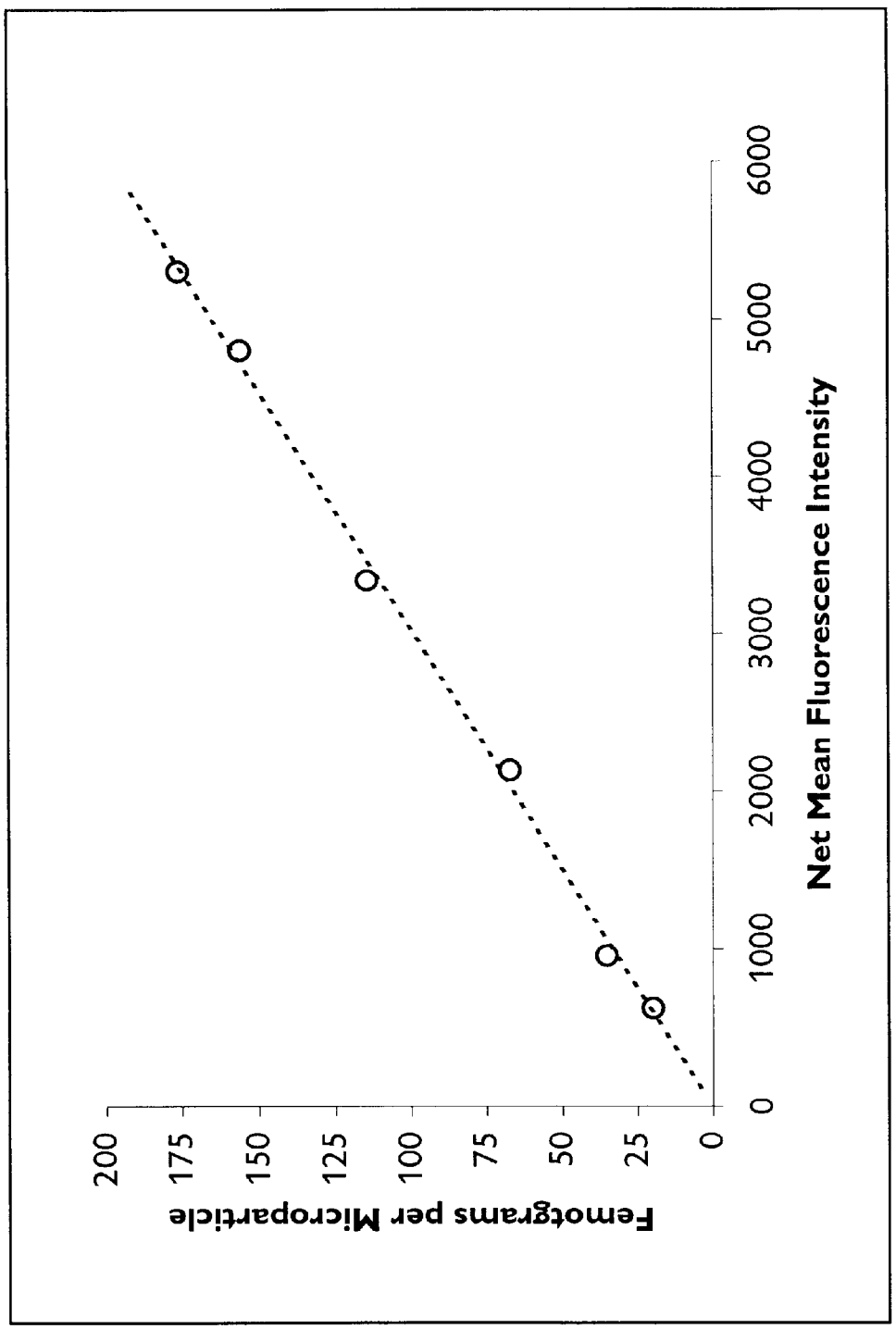
FIG. 4 shows a standard curve plot of six discrete femtogram (fg) concentrations of reference proteins (femtogram/microparticle on the Y axis) as a finction of fluorescence intensity (X vertical axis).

Examine the Coefficient of Variation reported for the subject microparticle replicates as an indication of protein immobilization homology (see for general steps of procedure in FIG. 3 and see for examples of analyte determination in the Table 1 shown below).

TABLE 1

| Protein Type | Coupling Type | Net Mean Fluorescence Intensity | Protein (femtograms/ Particle) | Protein MW Applied (Daltons) | Calculated Molecules/ Particle |
|---|---|---|---|---|---|
| Human IgG | Covalent | 6311.9 | 161.0 | 150000 | 6.46E + 05 |
| Human IgG | Adsorbed | 1927.3 | 49.1 | 150000 | 1.97E + 05 |
| Mouse IgG | Covalent | 4504.7 | 114.9 | 150000 | 4.61E + 05 |
| Mouse IgG | Adsorbed | 316.4 | 8.1 | 150000 | 3.24E + 04 |
| BSA | Covalent | 2936.5 | 74.9 | 60000 | 7.52E + 05 |
| BSA | Adsorbed | 1033.7 | 26.4 | 60000 | 2.65E + 05 |
| BGG | Covalent | 8245.9 | 210.3 | 150000 | 8.44E + 05 |
| BGG | Adsorbed | 447.4 | 11.4 | 150000 | 4.58E + 04 |
| Blank | NA | 18.5 | 0.5 | NA | NA |

Example 2

Preparation of Bovine Gamma Globulin (BGG) solid phase protein standards materials and equipment Sonicator bath; Microcentrifuge; Vortex; and Rotator. Bovine Gamma Globulin; Multiplex Microparticles, carboxylated, 5.6 μm diameter—8053, 8064, 8075, 8087, 9060, 9069, 9078, 9087; 1.5 ml microcentrifuge tube; Activation Buffer: 0.1M Sodium Phosphate, pH 6.2; Coupling: Phosphate Buffered Saline, pH 7.4; Wash Buffer: Phosphate Buffered Saline, pH 7.4, 0.05% Tween 20; Storage Buffer: Phosphate Buffered Saline, pH 7.4 with preservative; Sulfo NHS:N-Hydroxysulfosuccinimide sodium salt; and EDC:1-(3-dimethylaminopropyl)-3-ethyl-carbodimide hydrochloride.

Preparation

Allow all reagents to warm to room temperature. Dilute Bovine Gamma Globulin to 150, 60, 24, 10, 4, 2, 1 μg/ml in Coupling Buffer.

Solid phase activation

Figure 2:
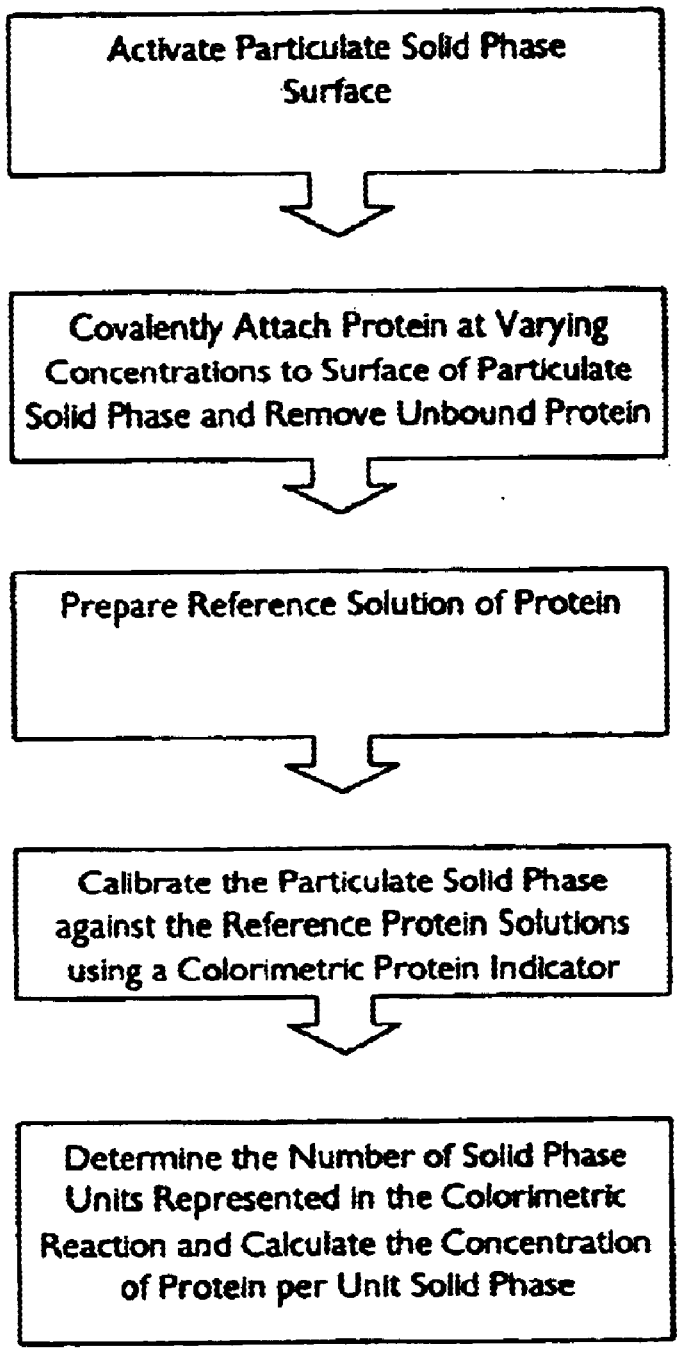
FIG. 2 shows a flow chart with sequential steps of making solid phase immobilized standards.

Aseptically dispense 1000 μl (50.0E+6 microspheres) of each type of Multiplex Microsphere stock (each number, e.g., 8053, refers to a flow cytometrically distinct set of beads) into its respective reaction tube (see following Table 2 and also FIG. 2).

TABLE 2

| Reaction Tube | Multiplex Microsphere Type |
|---|---|
| 0 | 8053 |
| A | 8064 |
| B | 8075 |
| C | 8087 |
| D | 9060 |
| E | 9069 |
| F | 9072 |
| G | 9087 |

Centrifuge reaction tubes for 60 seconds and aspirate supernatants. Add 400 μl of Activation Buffer to each reaction tube and sonicate until homogeneous distribution of microspheres is observed. Immediately before use add Activation Buffer to aliquot of Sulfo-NHS to make a 50 mg/ml solution and mix. Add 50 μl of the Sulfo-NHS solution to each microsphere suspension and mix with vortexing. Go immediately to next step. Add Activation Buffer to aliquot of EDC to make a 5.0 mg/ml solution and mix. Add 50 μl of the EDC solution for each microsphere suspension and mix with vortexing. Incubate for 20±2 min with rotation at room temperature in the dark. Harvest the activated microspheres with centrifugation for 60 seconds and aspirate supernatants while maintaining pellet orientation down. Wash activated microspheres twice with 1000 μl of Coupling Buffer with 60-second centrifugation steps. Go immediately to the protein coupling step.

Coupling of a protein to solid phase, washing, and storage

To initiate the coupling reaction add 500 μl of each Bovine Gamma Globulin preparation in Coupling Buffer to its respective reaction tube and mix with vortexing followed by sonication (see following Table 3).

TABLE 3

| Reaction Tube | Multiples Microsphere Type | BGG Coupling Concentration (μg/ml) |
|---|---|---|
| O | 8053 | 0 |
| A | 8064 | 1 |
| B | 8075 | 2 |
| C | 8087 | 4 |
| D | 9060 | 10 |
| E | 9069 | 24 |
| F | 9072 | 60 |
| G | 9087 | 150 |

Incubate for 2 hours with rotation at room temperature in the dark. Harvest the coupled microspheres with centrifugation for 60 at 10,000 g and aspirate the supernatants. Add 1000 μl of Wash Buffer and mix with vortexing followed by sonication. Incubate for 30 minutes with rotation at room temperature in the dark. Repeat steps 3 & 4 twice. Wash microspheres twice with 1000 μl of Storage Buffer with 60-second centrifugation steps. Suspend in 500 μl of Storage Buffer and transfer to a clean storage tube. Store refrigerated in a dark.

Example 3

Calibration of Bovine Gamma Globulin solid phase protein standards materials and equipment Microplate reader, 562 nm; Manifold, vacuum; and Shaking incubator, 37° C. Micro BCA Protein Assay Kit; Bovine Gamma Globulin Standard, stock solution; and Phosphate Buffered Saline (PBS), pH 7.4.

Preparation of solid phase standards

Allow Solid Phase BGG Immobilized Standard Preparations O, A, B, C, D, E, F, G, H to reach room temperature. Mix by vortexing followed by sonication. Remove approximately 20.0E+6 to 30.0E+6 microspheres in duplicate from each Solid Phase Standard Preparations and dispense into filter bottom microtiter wells. Also remove appropriate sample volume in duplicate for enumeration. Position filter bottom microtiter plate on vacuum manifold and apply low vacuum until well is drained. Re-suspend each particulate solid phase (microparticle) sample in 150 μl PBS.

Aqueous reference standards

Prepare aqueous Bovine Gamma Globulin (BGG) standards by diluting the BGG stock standard to 1, 3, 4, 6, 8, 12, 16, and 20 µg/ml in PBS. Dispense 150 µl of each standard in duplicate into the appropriate filter bottom microtiter wells.

Determination of the amount of protein bound to solid phase standards by an aqueous protein assay Add 150 µl of Working BCA Reagent to each well. Cover the plate and incubate the plate at 37° C. for 2 hours with shaking. Position a flat bottom microtiter plate in the vacuum manifold reservoir. Position filter bottom microtiter plate on the vacuum manifold and apply low vacuum to collect filtrate. Measure absorbance at 562 nm on a plate reader. Prepare a curve fit for the standards by plotting the average blank corrected absorbance reading for each standard versus its concentration in µg/ml. Interpolate the concentration of BGG (µg/ml) for each Solid Phase Standard Preparation and calculate the total BGG detected (µg). Divide the total BGG detected by the number of microspheres in the reaction to determine the amount of BGG per microsphere. The amount of BGG as expressed per microparticle is significantly smaller and is usually in attogram to femtogram range. While it is clear that very low concentrations in attogram range are easily detectable the lowest used level of BGG in this particular example is 770 attograms (see FIG. 2 and Table 4).

TABLE 4

| Microparticle Immobilized Protein Standards (femtogram/particle) | Net Mean Fluorescence Intensity |
| --- | --- |
| 0 | 0 |
| 0.77 | 30.1 |
| 19.7 | 677.6 |
| 40.1 | 1176.5 |
| 67.1 | 2621.0 |
| 114.3 | 4280.0 |
| 155.8 | 6277.2 |
| 175.8 | 6947.6 |

All cited references and patents are incorporated expressly hereinabove by way of reference.

While preferred embodiments of the invention have been illustrated and described, it is to be understood that, within the scope of the appended claims, various changes can be made therein. Hence, the invention can be practiced in ways other than those specifically described herein.

What is claimed is:

1. A process for determining the relative average amount of at least one protein of interest, which is immobilized on each of a plurality of particulate solid phases, comprising:
   (a) separately subjecting, under substantially the same labeling conditions, a plurality of particulate solid phases, to each of which is covalently immobilized an unknown average amount of at least one protein of interest, and a plurality of standard particulate solid phases to each of which is covalently immobilized a known average amount of at least one reference protein, to labeling conditions effective to provide protein of interest and reference protein both covalently labeled with at least one light-emitting label;
   (b) separating unbound label from the covalently labeled protein of interest and covalently labeled reference protein; and
   (c) comparing the average amount of light emitted by labels found on the standard particulate solid phases harboring the reference protein with that emitted by labels found on particulate solid phases harboring the protein of interest to provide a relative average amount of the protein of interest covalently immobilized on each of the particulate solid phases.

2. The process of claim 1 in which step (a) comprises subjecting a mixture comprising the particulate solid phases harboring the protein of interest and the standard particulate solid phases harboring the reference protein to a sufficient or excess amount of light-emitting label under conditions effective to provide labeled protein of interest and labeled reference protein.

3. The process of claim 1 in which a series of two or more standard particulate solid phases is utilized in the process, in which the two or more standard particulate solid phases harbor different known average amounts of at least one reference protein.

4. The process of claim 1 in which the at least one reference protein is the same as, similar to, analogous to, homologous to, or functionally equivalent to the protein of interest.

5. The process of claim 4 which permits the construction of a standard curve that permits the determination of the amount of the at least one reference protein or of the protein of interest based on the amount of light emitted by labels found on the standard particulate solid phase harboring the at least one reference protein or that emitted by labels found on the particulate solid phase harboring the protein of interest, as the case may be.

6. A method of quantifying the amount of at least one protein of interest immobilized directly or indirectly on a particulate solid phase comprising:
   (a) separately subjecting one or more particulate solid phases, to each of which is covalently immobilized directly or indirectly an unknown amount of at least one protein of interest, to labeling conditions effective to covalently affix to each particulate solid phase an amount of a light-emitting label which is proportional to the amount of the at least one protein of interest covalently immobilized to the particulate solid phase;
   (b) separating unbound label from the one or more covalently labeled particulate phases; and
   (c) relating the amount of light emitted from each particulate solid phase to the amount of the at least one protein of interest covalently immobilized to the particulate solid phase using a standard curve.

7. The method of claim 6 in which a standard curve is obtained by measuring the average amounts of light emitted by light-emitting labels affixed to a series of standard particulate solid phases harboring known average amounts of at least one reference protein labeled under labeling conditions similar to or substantially the same as those used in step (a) of claim 6.

8. The method of claim 7 in which the light-emitting label comprises a light-emitting dye.

9. The method of claim 8 in which the light-emitting dye includes an amine-reactive dye.

10. The method of claim 6 in which step (b) comprises measuring the amount of light emitted from each particulate solid phase using a flow analyzer.

11. The method of claim 6 which allows the determination of at least femtogram or at least attogram levels of the protein of interest.

12. A process for determining the presence or amount of an analyte of interest comprising:
   (a) providing a microparticle to which said analyte is covalently bound;
   (b) covalently labeling the microparticle-bound analyte with a light emitting label;

(c) separating unbound label from the covalently labeled microparticle-bound analyte; and (d) quantitating labeled analyte by comparing separately to a microparticle preparation standard carrying a known amount of a reference substance covalently labeled with said light-emitting label.

13. The process of claim 12, wherein the light-emitting label is an amine-reactive dye, which is bound to the analyte and the reference substance directly or indirectly via a linker.

14. The process of claim 12, wherein the microparticle further comprises at least one fluorescent dye, which is different from the light-emitting label.

15. The process of claim 12, wherein said quantitating step (c) is provided by a flow analyzer.

16. The process of claim 12, which allows determining at least femtogram or at least attogram amounts of the analyte.

17. A method of measuring the quantity of an analyte bound to a particulate solid phase, said method comprising the steps of:

(a) covalently associating the analyte with the particulate solid phase, said particulate solid phase having a fluorescent label embedded within or immobilized thereon, said label being capable of changing a fluorescence signal as a function of the concentration of the analyte;

(b) providing at least one standard microparticle preparation with the known amount of a reference protein covalently bound thereto, said standard microparticle preparation having the same fluorescent label as in step (a); and (c) separately measuring the quantity of the analyte covalently associated with the particulate solid phase by comparing the fluorescence signal of said particulate solid phase with the fluorescence signal of the standard microparticle preparation.

18. A process for determining the relative average amount of at least one protein of interest, which is immobilized on each of a plurality of particulate solid phases, comprising:

(a) subjecting, under substantially the same labeling conditions, a plurality of particulate solid phases, populations of which are distinguishable from one another to each of which is covalently immobilized an unknown average amount of at least one protein of interest, and a plurality of standard particulate solid phases, populations of which are distinguishable from one another to each of which is covalently immobilized a known average amount of at least one reference protein, to labeling conditions effective to provide protein of interest and reference protein both covalently labeled with at least one light-emitting label; and (b) comparing by multiplexed flow cytometry the average amount of light emitted by labels found on the standard particulate solid phases harboring the reference protein with that emitted by labels found on particulate solid phases harboring the protein of interest to provide a relative average amount of the protein of interest covalently immobilized on each of the particulate solid phases.

* * * * *